(12) United States Patent
Spear et al.

(10) Patent No.: US 8,629,294 B2
(45) Date of Patent: Jan. 14, 2014

(54) BORATE ESTERS, BORON-COMPRISING DOPANTS, AND METHODS OF FABRICATING BORON-COMPRISING DOPANTS

(75) Inventors: Richard A. Spear, Santa Cruz, CA (US); Edward W. Rutter, Jr., Pleasanton, CA (US); Lea M. Metin, San Jose, CA (US); Helen X. Xu, Sunnyvale, CA (US)

(73) Assignee: Honeywell International Inc., Morristown, NJ (US)

( * ) Notice: Subject to any disclaimer, the term of this patent is extended or adjusted under 35 U.S.C. 154(b) by 77 days.

(21) Appl. No.: 13/217,597

(22) Filed: Aug. 25, 2011

(65) Prior Publication Data

US 2013/0048918 A1 Feb. 28, 2013

(51) Int. Cl.
*C07F 5/04* (2006.01)

(52) U.S. Cl.
USPC .......................... 556/402; 556/400; 556/483

(58) Field of Classification Search
USPC .......................... 556/400, 402, 483
See application file for complete search history.

(56) References Cited

U.S. PATENT DOCUMENTS

| | | |
|---|---|---|
| 3,258,434 A | 6/1966 | Mackenzie et al. |
| 3,725,149 A | 4/1973 | Ilegems |
| 3,877,956 A | 4/1975 | Nitzche et al. |
| 3,960,605 A | 6/1976 | Beck et al. |
| 4,030,938 A | 6/1977 | Thomas |
| 4,072,636 A | 2/1978 | Ashida et al. |
| 4,102,766 A | 7/1978 | Fey |
| 4,104,091 A | 8/1978 | Evans, Jr. et al. |
| 4,236,948 A | 12/1980 | Seibold et al. |
| 4,243,427 A | 1/1981 | DiBugnara |
| 4,255,586 A | 3/1981 | Harrington et al. |
| 4,392,180 A | 7/1983 | Nair |
| 4,478,879 A | 10/1984 | Baraona et al. |
| 4,517,403 A | 5/1985 | Morel et al. |
| 4,548,741 A | 10/1985 | Hormadaly |
| 4,578,283 A | 3/1986 | Kirtley et al. |
| 4,707,346 A | 11/1987 | Hormadaly |
| 4,793,862 A | 12/1988 | Ishikawa et al. |
| 4,891,331 A | 1/1990 | Rapp |
| 4,927,770 A | 5/1990 | Swanson |
| 5,053,083 A | 10/1991 | Sinton |
| 5,152,819 A | 10/1992 | Blackwell et al. |
| 5,302,198 A | 4/1994 | Allman |
| 5,399,185 A | 3/1995 | Berthold et al. |
| 5,464,564 A | 11/1995 | Brown |
| 5,472,488 A | 12/1995 | Allman |
| 5,510,271 A | 4/1996 | Rohatgi et al. |
| 5,527,389 A | 6/1996 | Rosenblum et al. |
| 5,527,872 A | 6/1996 | Allman |
| 5,591,565 A | 1/1997 | Holdermann et al. |
| 5,614,018 A | 3/1997 | Azuma et al. |
| 5,618,766 A * | 4/1997 | Leiser et al. .................... 501/87 |
| 5,641,362 A | 6/1997 | Meier |
| 5,661,041 A | 8/1997 | Kano |
| 5,665,845 A | 9/1997 | Allman |
| 5,667,597 A | 9/1997 | Ishihara |
| 5,695,809 A | 12/1997 | Chadha et al. |
| 5,766,964 A | 6/1998 | Rohatgi et al. |
| 5,899,704 A | 5/1999 | Schlosser et al. |
| 5,928,438 A | 7/1999 | Salami et al. |
| 6,096,968 A | 8/2000 | Schlosser et al. |
| 6,099,647 A | 8/2000 | Yieh et al. |
| 6,143,976 A | 11/2000 | Endros |
| 6,162,658 A | 12/2000 | Green et al. |
| 6,180,869 B1 | 1/2001 | Meier et al. |
| 6,200,680 B1 | 3/2001 | Takeda et al. |
| 6,221,719 B1 | 4/2001 | Franco |
| 6,232,207 B1 | 5/2001 | Schindler |
| 6,251,756 B1 | 6/2001 | Horzel et al. |
| 6,262,359 B1 | 7/2001 | Meier et al. |
| 6,297,134 B1 | 10/2001 | Ui et al. |
| 6,300,267 B1 | 10/2001 | Chen et al. |
| 6,309,060 B1 | 10/2001 | Timmermans-Wang et al. |
| 6,355,581 B1 | 3/2002 | Vassiliev et al. |
| 6,384,317 B1 | 5/2002 | Kerschaver et al. |
| 6,429,037 B1 | 8/2002 | Wenham et al. |
| 6,479,885 B2 | 11/2002 | Buchanan et al. |

(Continued)

FOREIGN PATENT DOCUMENTS

| | | |
|---|---|---|
| CN | 101369612 | 2/2009 |
| CN | 101414647 A | 4/2009 |

(Continued)

OTHER PUBLICATIONS

Edwards, M., "Screen-Print Selective Diffusions for High-Efficiency Industrial Silicon Solar Cells", Progress in Photovoltaics: Research and Applications, vol. 16, Issue 1, Jan. 2008, pp. 31-45.

(Continued)

*Primary Examiner* — Johann R Richter
*Assistant Examiner* — Pancham Bakshi
(74) *Attorney, Agent, or Firm* — Ingrassia Fisher & Lorenz, PC

(57) ABSTRACT

Borate esters, boron-comprising dopants, and methods of fabricating boron-comprising dopants are provided herein. In an embodiment, a borate ester comprises boron and silicon wherein the boron is linked to the silicon by alkyl groups that are bonded via ester bonds with both the boron and the silicon. A method of fabricating a boron-comprising dopant comprises providing a borate and transesterifying the borate using a polyol-substituted silicon monomer.

13 Claims, 2 Drawing Sheets

(56) References Cited

U.S. PATENT DOCUMENTS

| | | |
|---|---|---|
| 6,518,087 B1 | 2/2003 | Furusawa et al. |
| 6,524,880 B2 | 2/2003 | Moon et al. |
| 6,552,414 B1 | 4/2003 | Horzel et al. |
| 6,632,730 B1 | 10/2003 | Meier et al. |
| 6,664,631 B2 | 12/2003 | Meier et al. |
| 6,695,903 B1 | 2/2004 | Kubelbeck et al. |
| 6,703,295 B2 | 3/2004 | Meier et al. |
| 6,737,340 B2 | 5/2004 | Meier et al. |
| 6,756,290 B1 | 6/2004 | Bultman |
| 6,773,994 B2 | 8/2004 | Chittipeddi et al. |
| 6,784,520 B2 | 8/2004 | Doi |
| 6,825,104 B2 | 11/2004 | Horzel et al. |
| 6,960,546 B2 | 11/2005 | Caspers et al. |
| 6,998,288 B1 | 2/2006 | Smith et al. |
| 7,029,943 B2 | 4/2006 | Kruhler |
| 7,041,549 B2 | 5/2006 | Ootsuka |
| 7,078,276 B1 | 7/2006 | Zurcher et al. |
| 7,078,324 B2 | 7/2006 | Dudek et al. |
| 7,097,788 B2 | 8/2006 | Kirkor et al. |
| 7,108,733 B2 | 9/2006 | Enokido |
| 7,115,216 B2 | 10/2006 | Carter et al. |
| 7,129,109 B2 | 10/2006 | Munzer et al. |
| 7,135,350 B1 | 11/2006 | Smith et al. |
| 7,144,751 B2 | 12/2006 | Gee et al. |
| 7,170,001 B2 | 1/2007 | Gee et al. |
| 7,186,358 B2 | 3/2007 | McCulloch et al. |
| 7,196,018 B2 | 3/2007 | Szlufcik et al. |
| 7,217,883 B2 | 5/2007 | Munzer |
| 7,230,057 B2 * | 6/2007 | Okumura et al. ............. 526/239 |
| 7,278,728 B2 | 10/2007 | Desie et al. |
| 7,332,445 B2 | 2/2008 | Lukas et al. |
| 7,335,555 B2 | 2/2008 | Gee et al. |
| 7,393,464 B2 | 7/2008 | Wenderoth et al. |
| 7,393,723 B2 | 7/2008 | Yamazaki et al. |
| 7,402,448 B2 | 7/2008 | Narayanan et al. |
| 7,456,084 B2 | 11/2008 | Jonczyk et al. |
| 7,459,391 B2 | 12/2008 | Yoshizawa et al. |
| 7,468,485 B1 | 12/2008 | Swanson |
| 7,537,951 B2 | 5/2009 | Gambino et al. |
| 7,559,494 B1 | 7/2009 | Yadav et al. |
| 7,572,740 B2 | 8/2009 | Terry et al. |
| 7,615,393 B1 | 11/2009 | Shah et al. |
| 7,633,006 B1 | 12/2009 | Swanson |
| 7,635,600 B2 | 12/2009 | Zhang et al. |
| 7,638,438 B2 | 12/2009 | Eldershaw |
| 7,867,960 B2 | 1/2011 | Yamaguchi et al. |
| 8,053,867 B2 | 11/2011 | Huang et al. |
| 8,138,070 B2 | 3/2012 | Kelman et al. |
| 2002/0046765 A1 | 4/2002 | Uematsu et al. |
| 2002/0153039 A1 | 10/2002 | Moon et al. |
| 2003/0134469 A1 | 7/2003 | Horzel et al. |
| 2003/0153141 A1 | 8/2003 | Carter et al. |
| 2004/0028971 A1 | 2/2004 | Wenderoth et al. |
| 2004/0063326 A1 | 4/2004 | Szlufcik et al. |
| 2004/0112426 A1 | 6/2004 | Hagino |
| 2004/0242019 A1 | 12/2004 | Klein et al. |
| 2004/0261839 A1 | 12/2004 | Gee et al. |
| 2004/0261840 A1 | 12/2004 | Schmit et al. |
| 2005/0014359 A1 | 1/2005 | Segawa et al. |
| 2005/0189015 A1 | 9/2005 | Rohatgi et al. |
| 2005/0190245 A1 | 9/2005 | Desie et al. |
| 2005/0268963 A1 | 12/2005 | Jordan et al. |
| 2006/0060238 A1 | 3/2006 | Hacke et al. |
| 2006/0105581 A1 | 5/2006 | Bielfeld et al. |
| 2006/0162766 A1 | 7/2006 | Gee et al. |
| 2006/0163744 A1 | 7/2006 | Vanheusden et al. |
| 2006/0166429 A1 | 7/2006 | Chaudhry et al. |
| 2006/0222869 A1 | 10/2006 | Cai et al. |
| 2006/0237719 A1 | 10/2006 | Colfer et al. |
| 2006/0258820 A1 | 11/2006 | Schneider |
| 2007/0012355 A1 | 1/2007 | LoCascio et al. |
| 2007/0034251 A1 | 2/2007 | Jonczyk et al. |
| 2007/0075416 A1 | 4/2007 | Anderson et al. |
| 2007/0151598 A1 | 7/2007 | De Ceuster et al. |
| 2007/0157965 A1 | 7/2007 | Park |
| 2007/0215203 A1 | 9/2007 | Ishikawa et al. |
| 2007/0269923 A1 | 11/2007 | Lee et al. |
| 2007/0290283 A1 | 12/2007 | Park et al. |
| 2008/0024752 A1 | 1/2008 | Ng et al. |
| 2008/0026550 A1 | 1/2008 | Werner et al. |
| 2008/0036799 A1 | 2/2008 | Ittel |
| 2008/0042212 A1 | 2/2008 | Kamath et al. |
| 2008/0044964 A1 | 2/2008 | Kamath et al. |
| 2008/0048240 A1 | 2/2008 | Kamath et al. |
| 2008/0058231 A1 | 3/2008 | Yamaguchi et al. |
| 2008/0058232 A1 | 3/2008 | Yamaguchi et al. |
| 2008/0064813 A1 | 3/2008 | Schneider |
| 2008/0076240 A1 | 3/2008 | Veschetti et al. |
| 2008/0092944 A1 | 4/2008 | Rubin |
| 2008/0107814 A1 | 5/2008 | Wierer et al. |
| 2008/0107815 A1 | 5/2008 | Schneider et al. |
| 2008/0119593 A1 | 5/2008 | Stramel et al. |
| 2008/0121279 A1 | 5/2008 | Swanson |
| 2008/0138456 A1 | 6/2008 | Fork et al. |
| 2008/0142075 A1 | 6/2008 | Reddy et al. |
| 2008/0160733 A1 | 7/2008 | Hieslmair et al. |
| 2008/0199687 A1 | 8/2008 | Chiruvolu et al. |
| 2008/0202576 A1 | 8/2008 | Hieslmair |
| 2008/0210298 A1 | 9/2008 | Kuebelbeck et al. |
| 2008/0241986 A1 | 10/2008 | Rohatgi et al. |
| 2008/0241987 A1 | 10/2008 | Rohatgi et al. |
| 2008/0241988 A1 | 10/2008 | Rohatgi et al. |
| 2008/0251121 A1 | 10/2008 | Stone |
| 2008/0264332 A1 | 10/2008 | Sepehry-Fard |
| 2008/0268584 A1 | 10/2008 | Anderson et al. |
| 2008/0290368 A1 | 11/2008 | Rubin |
| 2008/0314288 A1 | 12/2008 | Biro et al. |
| 2009/0007962 A1 | 1/2009 | Wenham et al. |
| 2009/0007965 A1 | 1/2009 | Rohatgi et al. |
| 2009/0017606 A1 | 1/2009 | Fath et al. |
| 2009/0020156 A1 | 1/2009 | Ohtsuka et al. |
| 2009/0020829 A1 | 1/2009 | Chandra et al. |
| 2009/0068474 A1 | 3/2009 | Lower et al. |
| 2009/0068783 A1 | 3/2009 | Borden |
| 2009/0084440 A1 | 4/2009 | Wang et al. |
| 2009/0142565 A1 | 6/2009 | Takahashi et al. |
| 2009/0142875 A1 | 6/2009 | Borden et al. |
| 2009/0142911 A1 | 6/2009 | Asano et al. |
| 2009/0149554 A1 | 6/2009 | Ishikawa et al. |
| 2009/0183768 A1 | 7/2009 | Wenham et al. |
| 2009/0194153 A1 | 8/2009 | Hilaii et al. |
| 2009/0226609 A1 | 9/2009 | Boisvert et al. |
| 2009/0227061 A1 | 9/2009 | Bateman et al. |
| 2009/0227097 A1 | 9/2009 | Bateman et al. |
| 2009/0233426 A1 | 9/2009 | Poplavskyy et al. |
| 2009/0239330 A1 | 9/2009 | Vanheusden et al. |
| 2009/0239363 A1 | 9/2009 | Leung et al. |
| 2009/0260684 A1 | 10/2009 | You |
| 2009/0292053 A1 | 11/2009 | Morita |
| 2009/0308440 A1 | 12/2009 | Adibi et al. |
| 2009/0314341 A1 | 12/2009 | Borden et al. |
| 2009/0314344 A1 | 12/2009 | Fork et al. |
| 2010/0016200 A1 | 1/2010 | Nagare et al. |
| 2010/0068848 A1 | 3/2010 | Kuo et al. |
| 2010/0175744 A1 | 7/2010 | Hirai et al. |
| 2010/0261347 A1 | 10/2010 | Nobutoh |
| 2010/0319771 A1 | 12/2010 | Mihailetchi et al. |
| 2011/0021012 A1 | 1/2011 | Leung et al. |
| 2011/0021736 A1 | 1/2011 | Zhu |
| 2011/0045624 A1 | 2/2011 | Tsukigata et al. |
| 2011/0195541 A1 | 8/2011 | Machii et al. |
| 2011/0240997 A1 | 10/2011 | Rockenberger et al. |
| 2011/0256658 A1 | 10/2011 | Machii et al. |
| 2012/0006393 A1 | 1/2012 | Cruz et al. |
| 2012/0115980 A1 * | 5/2012 | Vanderlaan et al. .......... 523/107 |
| 2012/0222734 A1 | 9/2012 | Kano et al. |

FOREIGN PATENT DOCUMENTS

| | | |
|---|---|---|
| CN | 101777606 A | 7/2010 |
| CN | 101937940 A | 1/2011 |
| CN | 102097525 A | 6/2011 |
| CN | 102057466 A | 8/2011 |
| CN | 102263159 A | 11/2011 |

(56) References Cited

FOREIGN PATENT DOCUMENTS

| | | | |
|---|---|---|---|
| EP | 0195148 A1 | 9/1986 | |
| EP | 0381430 A2 | 1/1990 | |
| EP | 485122 A1 | 5/1992 | |
| EP | 0890980 A2 | 1/1999 | |
| EP | 999598 A1 | 5/2000 | |
| EP | 1024523 A1 | 8/2000 | |
| EP | 0770265 B1 | 3/2002 | |
| EP | 1843389 A1 | 10/2007 | |
| EP | 1876651 A1 | 1/2008 | |
| GB | 1250585 | 10/1971 | |
| JP | 09036853 A | 11/1997 | |
| JP | 2003188393 A | 4/2003 | |
| JP | 2003168807 | 6/2003 | |
| JP | 2003168810 | 6/2003 | |
| JP | 2003188393 A | 7/2003 | |
| JP | 2003224285 | 8/2003 | |
| JP | 2004221149 | 8/2004 | |
| JP | 2005038997 | 2/2005 | |
| JP | 2006-265415 | * 10/2006 | ............ C08G 59/70 |
| JP | 2007081300 | 3/2007 | |
| JP | 2011187894 A2 | 9/2011 | |
| KR | 1019890016644 A | 11/1989 | |
| KR | 19990066346 A1 | 8/1999 | |
| KR | 101054985 B1 | 8/2011 | |
| KR | 101165915 B1 | 7/2012 | |
| WO | 9715075 | 4/1997 | |
| WO | 2006029250 A2 | 3/2006 | |
| WO | 2006131251 A1 | 12/2006 | |
| WO | 2007059577 A1 | 5/2007 | |
| WO | 2007059578 A1 | 5/2007 | |
| WO | 2007106502 A2 | 9/2007 | |
| WO | 2007111996 A2 | 10/2007 | |
| WO | 2007118121 A2 | 10/2007 | |
| WO | 2007129966 A1 | 11/2007 | |
| WO | 2008039078 A2 | 4/2008 | |
| WO | 2008054473 A2 | 5/2008 | |
| WO | 2008085806 A1 | 7/2008 | |
| WO | 2008098407 A1 | 8/2008 | |
| WO | 2008141415 A1 | 11/2008 | |
| WO | 2009010585 A2 | 1/2009 | |
| WO | 2009013307 A2 | 1/2009 | |
| WO | 2009032359 A2 | 3/2009 | |
| WO | 2009052511 A2 | 4/2009 | |
| WO | 2009067005 A1 | 5/2009 | |
| WO | 2009085224 A2 | 7/2009 | |
| WO | 2009088138 A1 | 7/2009 | |
| WO | 2009094575 A2 | 7/2009 | |
| WO | 2009107920 A1 | 9/2009 | |
| WO | 2009116569 A1 | 9/2009 | |
| WO | 2009126803 A2 | 10/2009 | |
| WO | 2009152378 A1 | 12/2009 | |
| WO | 2010089654 A1 | 8/2010 | |

OTHER PUBLICATIONS

Salami, J. "Diffusion Paste Development for Printable IBC and Bifacial Silicon Solar Cells", Conference Record of the 2006 IEEE 4th World Conference on Photovoltaic Energy Conversion, WCPEC-4, vol. 2, 2007, Article No. 4059888, pp. 1323-1325.
Horzel, J., "A simple processing sequence for selective emitters (Si solar cells]," Photovoltaic Specialists Conference, 1997, Conference Record of the Twenty-Sixth IEEE; Sep. 29-Oct. 3, 1997; pp. 139-142; Meeting Date: Sep. 29, 1997-Oct. 3, 1997.
Accuglass P-114A Spin-On Glass, Material Safety Data Sheet, HW International, Oct. 29, 2003, pp. 1-6.
Accuglass P-5S, Product Bulletin, Thin-Film Dielectrics, HW International, 2002, pp. 1-2.
Accuglass P-TTY A series Phosphosilicate Spin-On Glasses, Allied Signal, Inc. Planarization and Diffusion Products, May 1992, pp. 1-2.
Accuglass P-TTY Product Bulletin, Thin-Film Dielectrics, HW International, 2002, pp. 1-2.
Accuglass P-XXY Spin-On Glass, Material Safety Data Sheet, HW International, May 14, 2003, pp. 1-7.
Diffusion Technology Phosphorus Spin-On Dopants P-8 Series (P-8545, P-854 (:1), Material Safety Data Sheet, HW International, Apr. 25, 2003, p. 1-7.
Techniglas Technical Products, Boron Plus, Product Information. pp. 1-3, 2008.
BoronPlus, High Purity Planar Dopants, ISO Certified 3002/14001, Techneglas Technical Products, 2000.
Zable, J.L., Splatter During Ink Jet Printing, IBM J. Res. Develop., Jul. 1977, pp. 315-320.
B-30, B-40, B-50, B-60 Spin-On Dopants, Material Safety Data Sheet, Honeywell International, Apr. 29, 2003, pp. 1-7.
Accuspin Boron; Polymers for All P-Type Diffusion, Honeywell International, 2005, pp. 1-2.
Spin-On Dopants, Thin Film—Dielectrics, Application Comparision, Honeywell International, 2002, pp. 1-2.
Tonooka, K., et al., "Fluorescent Properties of Tb-doped Borosilicate Glass Films Prepared by a Sol-gel Method," Proceedings of SPIE—The International Society for Optical Engineering, v 4282, p. 193-199, 2001.
Ruge, Ingolf et al. "Halbleiter Technologie," Publication: Berlin; New York : Springer-Verlag; Edition: 2., überarbeitete und erw. Aufl. / von Hermann Mader. Year: 1984; Description: 404 p. : 218 ill. ; 24 cm.; Language: German; Series: Halbleiter-Elektronik ; Bd. 4; Variation: Halbleiter-Elektronik ;; Bd. 4. Standard No. ISBN: 0387126619 (U.S.); 9780387126616 (U.S.); 3540126619; 9783540126614; National Library: 831027150 LCCN: 85-106745.
Un, Y., et al., "Behavior of Various Organosilicon Molecules in PECVD Processes for Hydrocarbon-doped Silicon Oxide Films Diffusion and Defect Data Pt.B," Solid State Phenomena, v 124-126, n Part 1, p. 347-350, 2007, Advances in Nanomaterials and Processing—IUMRS.
Takeda, S., et al., "Surface Modification of Sputtered SiO2 Thin Films by Metal Doping," Materials Research Society Symposium—Proceedings, v 750, p. 443-448, 2002.
Sabbah, H., "Thermal Grafting of Fluorinated Molecular Monolayers on Doped Amorphous Silicon Suffaces," Journal of Applied Physics, v 105, n 6, 2009.
Popov, V.P., et al., "Atomically Flat Surface of Hydrogen Transferred Si Film with Boron Delta Doped Layer," Meeting Abstracts, p. 526, 2005, 207th Meeting of the Electrochemical Society—Meeting Abstracts.
Osada, Yoshito, et al., "Plasma-polymerized Organosilioxane Membranes Prepared by Simultaneous Doping of 2 Molecules and the Effect on Liquid Permeability," Journal of Polymer Science, Part A-1, Polymer Chemistry, v 23, n 9, p. 2425-2439, Sep. 1985.
Li, Jiangtian, et al. "A Pre-modification-direct Synthesis Route for the Covalent Incorporation and Monomeric Dispersion of Hydrophobic Organic Chromophores, in Mesoporous Silica Films," Microporous and Mesoporous Materials, v 111, n 1-3, p. 150-156, Apr. 15, 2008.
The Written Opinion and International Search Report mailed Feb. 1, 2013 in International Application No. PCT/US2012/051786.
International Search Report and Written Opinion mailed May 24, 2012 in International Application No. PCT/CN2011/001392.
Wang, C., et al., Photophysical Properties of Rare Earth (Eu3+, Sm3+, Tb3+) Complex Covalently Immobilized in Hybrid Si-O-B Xerogels, Journal of Fluorescence, 2011, pp. 1-9.
Smirnovam, I., et al., Investigation into the Surface Morphology of Nanosized Silicate and Hybrid Films by Optical and Atomic-Force Microscopy, Glass Physics and Chemistry, vol. 33, No. 4, 2007, pp. 306-314.
The Written Opinion and International Search Report mailed Feb. 22, 2013 in International Application No. PCT/US2012/051719.
The Written Opinion and International Search Report mailed Mar. 25, 2013 in International Application No. PCT/US2012/059847.

* cited by examiner

BORATE ESTERS, BORON-COMPRISING DOPANTS, AND METHODS OF FABRICATING BORON-COMPRISING DOPANTS

TECHNICAL FIELD

The present invention generally relates to dopants and methods of fabricating dopants, and more particularly relates to borate esters, boron-comprising dopants, and methods of fabricating boron-comprising dopants.

BACKGROUND

Doping of semiconductor materials with conductivity-determining type impurities, such as n-type and p-type elements, is used in a variety of applications that require modification of the electrical characteristics of the semiconductor materials. Boron is conventionally used to form p-type regions in a semiconductor material.

Some doping applications require patternized p-type (p+) regions to form advanced devices such as interdigital back contact (IBC), local back surface field (LBSF), or selective emitter (SE) solar cells. Other applications need global coverage such as for emitters for N-type (n+) solar cells or back surface fields (BSF) for p+ solar cells.

Boron-comprising dopants can be deposited to form specific patterns using application processes such as screen printing, spray application, spin coating, rotogravure application, inkjet printing, and the like. Screen printing involves the use of a patterned screen or stencil that is disposed over a semiconductor material. A liquid dopant is placed on top of the screen and is mechanically pressed through the screen to deposit on the semiconductor material (e.g. solar wafer). If the screen has a pattern formed by areas that have no pores and areas that do have pores, the material can be deposited in a pattern that corresponds to the pattern of the screen. Spin application involves spinning the semiconductor material at a high spin speed such as, for example, up to 1200 revolutions per minute or even higher, while spraying the liquid dopant onto the spinning semiconductor material at a desired fluid pressure. Spinning causes the liquid dopant to spread outward substantially evenly across the semiconductor material. The liquid dopant also can be sprayed onto a semiconductor material at a desired fluid pressure at a position substantially at the center of the semiconductor material. The fluid pressure causes the dopant to spread radially and substantially evenly across the wafer. Rotogravure printing involves a roller upon which is engraved a pattern. The liquid dopant is applied to the engraved pattern of the roller, which is pressed against a semiconductor material and rolled across the semiconductor material, thereby transferring the liquid dopant to the semiconductor material according to the pattern on the roller. Inkjet printing refers to a non-contact printing process whereby a fluid is projected from a nozzle directly onto a substrate to form a desired pattern. Each of the various application processes described above utilizes a dopant formulation with a viscosity and polarity suitable for the given process. For example, screen printing requires relatively high viscosity while inkjet printing requires a viscosity low enough so that the dopant can be dispensed from a nozzle.

Boron siloxane and boron silicate dopants are often used in the above-described application processes and are typically made by sol-gel processes using polymers and oligomers. However, these dopants suffer from a number of drawbacks. For example, when produced using a sol-gel process, such conventional materials typically do not exhibit relatively high viscosity. Because of the low viscosity, "thickeners" are required, which must be removed during subsequent processing leading to additional challenges. Further, the molecular weight of such dopants is unstable, increasing at room temperature. Accordingly, the dopants typically must be transported, used, and stored under refrigeration. In addition, the dopants can be formed with pockets or regions of high boron concentration or high silicon concentration that can adversely affect the material or electrical characteristics of the post-diffusion electrical devices. Moreover, fabrication of the dopants requires the use of solvents that can be volatile and flammable, thus requiring expensive engineering and safety controls. And the fabrication process utilizes polymers and oligomers mixed directly in a solvent (or solvent mixture) that is limited by its suitability for the polymerization reaction. Further, instability of the sol-gel material and volatility of the solvent could dry and clog the printing apparatus. For example, such drying and clogging can result in a short "pot life" of a screen printer. Typically, it is preferable in high volume manufacture processes to have a "pot life" of a screen printer of over eight hours to avoid changing screens between personnel shifts.

Accordingly, it is desirable to provide borate esters and boron-comprising dopants that can be formulated using polyol-substituted silicon monomers. It is also desirable to provide borate esters and boron-comprising dopants that can be fabricated with variable viscosities with molecular weights that can exhibit stability during use and storage. In addition, it is desirable to provide methods for fabricating boron-comprising dopants. Furthermore, other desirable features and characteristics of the present invention will become apparent from the subsequent detailed description of the invention and the appended claims, taken in conjunction with the accompanying drawings and this background of the invention.

BRIEF SUMMARY

Borate esters, boron-comprising dopants, and methods for fabricating boron-comprising dopants are provided herein. In accordance with an exemplary embodiment, a borate ester comprises boron and silicon wherein the boron is linked to the silicon by alkyl groups that are bonded via ester bonds with both the boron and the silicon.

In accordance with another embodiment, a boron-comprising dopant comprises a boron and silicon network wherein boron and silicon are connected via Si—O-alkyl group-O—B linkages.

A method of fabricating a boron-comprising dopant in accordance with an exemplary embodiment is provided. The method comprises providing a borate and transesterifying the borate using a polyol-substituted silicon monomer.

BRIEF DESCRIPTION OF THE DRAWINGS

The present invention will hereinafter be described in conjunction with the following drawing figures, wherein like numerals denote like elements, and wherein.

DETAILED DESCRIPTION

The following detailed description is merely exemplary in nature and is not intended to limit the invention or the application and uses of the invention. Furthermore, there is no intention to be bound by any theory presented in the preceding background or the following detailed description.

Borate esters, boron-comprising dopants, and methods of fabricating boron-comprising dopants are provided herein. The borate esters and boron-comprising dopants are fabricated by the transesterification of borate using polyol-substituted silicon monomers forming a boron and silicon network. Because the ester and dopant are formed using silicon monomers as opposed to polymers or oligomers used in conventional dopants, the synthesis of the ester and dopant is simple and the viscosity of the ester and dopant can be controlled and varied from less than 2 centipoise (cP) to over 100,000 cP. By manipulating the mole ratio of silicon to boron, the viscosity and polarity can be controlled so that the dopant is suitable for a particular method of doping application, such as screen printing, spin coating, inkjet printing, spray application, roller application, and the like. The boron also is in a non-volatile form, being polymerized into the Si-ester network, with minimal "outgassing", that is, vaporization or diffusion from the dopant to the atmosphere, but provides for maximum doping efficiency. The boron and silicon are dispersed evenly throughout the ester network without pockets of high boron concentration or high silicon concentration. In addition, the molecular weight is stable at room temperature and, thus, the dopant can be used, transported, and stored at room temperature. Further, compared to sol-gel processing, the methods contemplated herein are simple and less costly.

Figure 1:
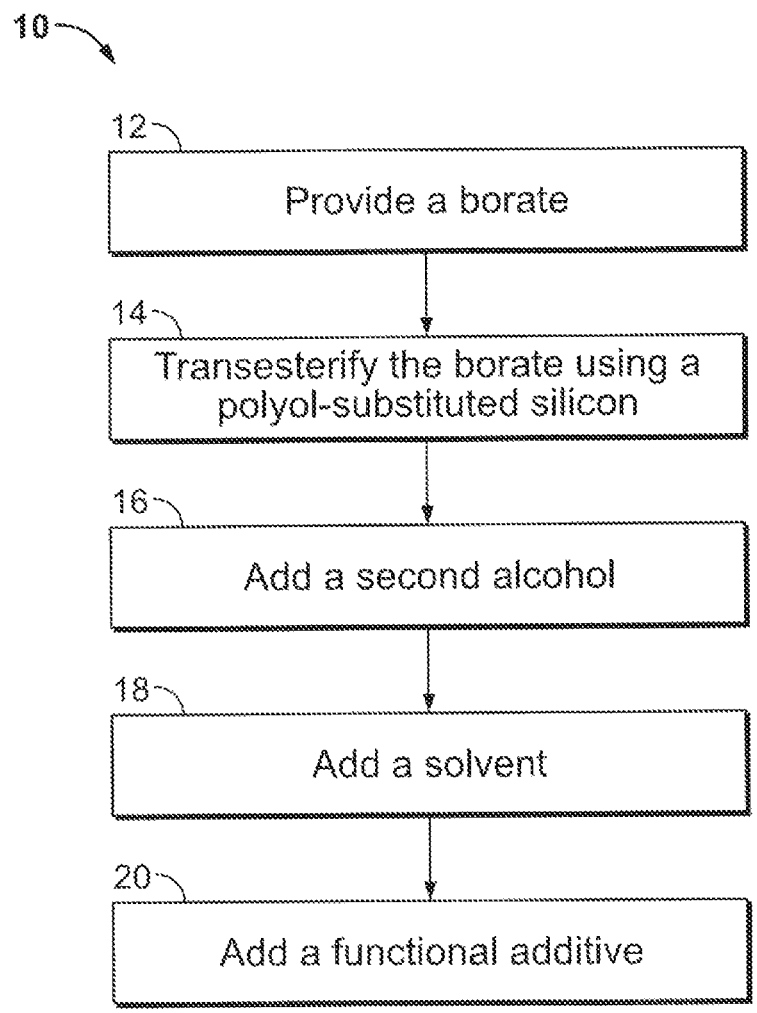
FIG. 1 is a flowchart of a method for fabricating a borate ester and boron-comprising dopant in accordance with an exemplary embodiment.

FIG. 1 illustrates a method 10 of fabricating a boron-comprising dopant in accordance with an exemplary embodiment. The method 10 includes providing a borate (step 12). The borate may be any salt or ester of boric acid. In one embodiment, however, the ester group of the borate is a branched or unbranched carbon chain with no fewer than 3 carbons. Alkyl moieties smaller than this are known to azeotrope; ethyl borate, for example, vaporizes under the same temperature/pressure conditions as ethanol. In a preferred embodiment, the borate is tributyl borate, tripropylene glycol methyl ether borate, or a combination thereof. Branched or unbranched alkyls with carbon chains having more than four carbons also may be used.

The method 10 continues with the transesterification of the borate achieved by combining the borate with a polyol-substituted silicon monomer (step 14). The polyol-substituted silicon can be any tetra-, tri-, di-, or mono-siloxane species with pendant —OH groups including triesters, diesters, and monoesters. Examples of suitable polyols include, but are not limited to, pentaerythritol, pentane diol, glycerol, ethylene glycol, butane diol, and the like, and combinations thereof. In a preferred embodiment, the polyol-substituted silicon is tetrakis(2-hydroxyethoxy)silane, tetrakis(2-hydroxypropoxy)silane, tetra(2-hydroxybutoxy)silane, tetrakis(hydroxypentoxy)-silane, or combinations thereof. The borate and the polyol-substituted silicon are combined using any suitable mixing or stirring process that forms a homogeneous solution. For example, a low speed sonicator or a high shear mixing apparatus, such as a homogenizer, a microfluidizer, a cowls blade high shear mixer, an automated media mill, or a ball mill, may be used for several seconds to an hour or more to form the borate ester and the boron-comprising dopant. Transesterification can occur at room temperature (18.3° C. (65° F.) to 29.4° C. (85° F.)), although a higher temperature may be utilized depending on the molecular weight of the polyol-substituted silicon. For example temperatures in the range of from 18° C. to about 125° C. may be used. The resulting borate ester is a network comprising borate(s) linked to silicate(s) of the form:

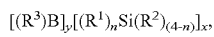

$[(R^3)B]_y[(R^1)_nSi(R^2)_{(4-n)}]_x$, where $R^1$ is any diol or polyol or combination thereof, $R^2$ is any alkyl, aromatic, alkoxy, or phenoxy group, $R^3$ is tripropylene glycol butyl ether, heptanol, hexanol, propylene glycol methyl ether (PGME), dipropylene glycol methyl ether, di-propylene glycol propyl ether, di-propylene glycol butyl ether, butanol, pentanol, octanol, or decanol, n is 1, 2, 3, or 4, and x/y is equal to a value between 0.75 to 6.

Figure 2:
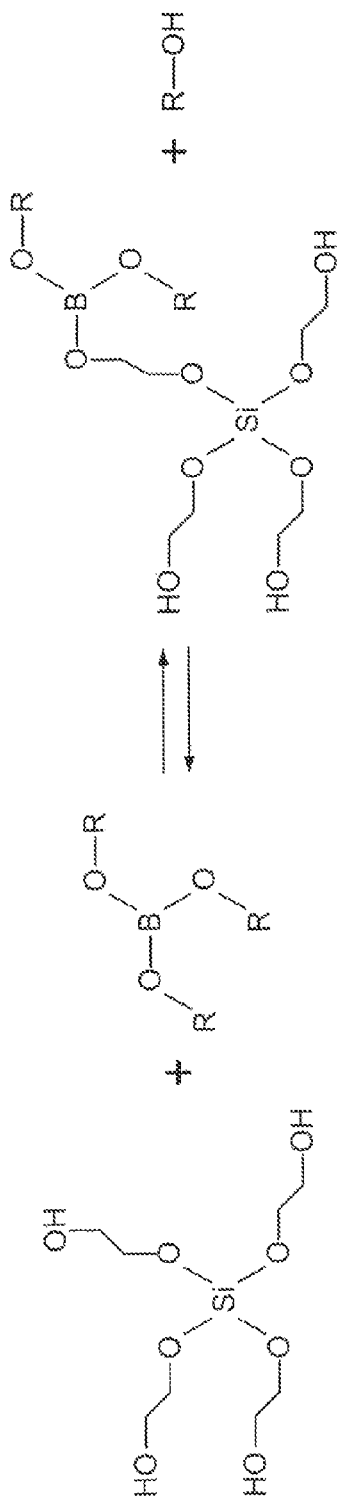
FIG. 2 is an illustration of borate ester formed by the transesterification of a trialkyl borate using tetrakis(2-hydroxyethoxy)silane.

FIG. 2 is a schematic illustration of a chemical mechanism by which the transesterification of the borate occurs. As illustrated in FIG. 2, the resulting products include a primary alcohol ROH and the borate ester. During transesterification, the boron of the borate and the silicon of the polyol-substituted silicon are linked by the alkyl group of the polyol. The polyol forms ester bonds with the boron and the silicon to form the borate ester. The —OR ester moieties of the borate bond to the hydrogen molecules of the polyol to form the primary ROH alcohol. As the reaction continues, the borate ester forms a boron and silicon network in which the boron and silicon are connected via Si—O-alkyl group-O—B linkages, the alkyl group derived from the polyol. While, for illustration purposes, the polyol-substituted silicon is tetrakis(2-hydroxyethoxy)silane, it will be appreciated that the invention is not so limited and any suitable polyol-substituted silicon monomer may be used.

The viscosity and the polarity of the borate ester and/or the boron-comprising dopant can be adjusted by manipulating the mole ratio of silicon to boron. As the amount of boron decreases in the dopant, the amount of Si—O-alkyl group-O—B linkages decrease and the effective molecular weight of the dopant decreases. Accordingly, the viscosity of the dopant decreases. In one embodiment, the mole ratio ranges from about 0.75:1 Si:B to about 6:1 Si:B. In a preferred embodiment, the mole ratio ranges from about 1.5:1 Si:B to about 3:1 Si:B.

Figure 3:
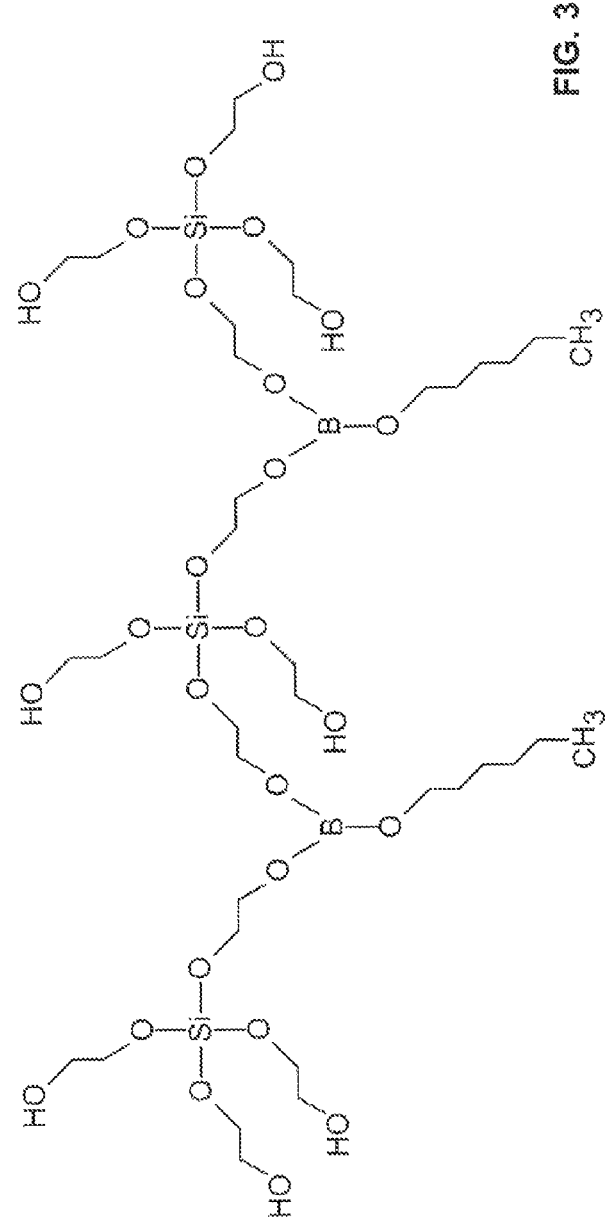
FIG. 3 is an illustration of a borate ester formed from tetrakis(2-hydroxyethoxy)silane, tributyl borate, and 1-hexanol.

Referring back to FIG. 1, in an exemplary embodiment, a second alcohol may be added to the polyol-substituted silicon and the borate to adjust the viscosity and polarity of the resulting dopant (step 16). The ester bonds on the borate molecule are labile and exchange alcohols freely. Accordingly, the second alcohol changes the molecular weight of the resulting borate ester and, hence, its viscosity, by forming an ester bond with the boron molecule. FIG. 3 is an illustration of the molecular structure of a borate ester formed from tetrakis(2-hydroxyethoxy)silane, tributyl borate and 1-hexanol. As evident from FIG. 3, the boron and silicon molecules are linked via the alkyl group of the polyol and the remaining butyl ester moiety bonded to the boron is replaced by a hexane ester moiety. The second alcohol can be any alcohol that can form an ester bond with the boron molecule. In one embodiment, for reasons of processing convenience, the second alcohol is one that has a boiling point that is significantly different from the primary alcohol so that the primary alcohol can be selectively removed from the dopant. In another embodiment, the second alcohol is added in an amount that is sufficient to change the borate ester viscosity to a desirable value but is not so large that it interferes with the Si—O-alkyl group-O—B linkages, thus breaking up the borate ester network. Examples of suitable second alcohols include, but are not limited to, tripropylene glycol butyl ether (TPnB), dipropylene glycol methyl ether, heptanol, hexanol, amyl alcohol, octanol, decanol, dodecanol, methoxypropanol, and the like, and combinations thereof. It will be appreciated that, during the processing, the second alcohol may be added first to the polyol-substituted silicon, first to the borate, or to the mixture of the polyol-substituted silicon and borate. Preferably, the second alcohol is combined with the reactants at a temperature that permits the primary alcohol to be evaporated from the dopant but permits the second alcohol to react with the borate.

In another embodiment, the method comprises adding a solvent to the polyol-substituted silicon, the borate, or a mixture thereof (step 18). The presence of the solvent allows for the adjustment of the viscosity of the dopant so that the dopant has a desired viscosity suitable for a particular application process. Solvents suitable for use comprise any suitable pure fluid or mixture of fluids that is capable of forming a solution with the borate ester. In some contemplated embodiments, the solvent or solvent mixture comprises aliphatic, cyclic, and aromatic hydrocarbons. Contemplated hydrocarbon solvents include alkanes, such as heptane, nonane, octane, dodecane, 2-methylbutane, hexadecane, tridecane, pentadecane, cyclopentane, 2,2,4-trimethylpentane, petroleum ethers, halogenated hydrocarbons, such as chlorinated hydrocarbons, siloxane solvents such as hexamethyl disiloxane, octamethyl cyclotetrasiloxane, decamethyl cyclopentasiloxane, isobutylbenzene, tetraethylorthosilicate, tetrakis(methyoxyethoxyethoxy)silane, tetrakis(methoxyethoxy)silane, tetrakis(ethoxyethoxy)silane, and tetrakis(2-ethylhexoxy)silane.

In other contemplated embodiments, the solvent or solvent mixture may comprise those solvents that are not considered part of the hydrocarbon solvent family of compounds, such as alcohols, ketones (such as acetone, diethylketone, methylethylketone, and the like), esters, ethers, amides and amines. Examples of solvents suitable for use during formation of the dopant include, but are not limited to, propylene glycol methyl ether (PGME), propylene glycol monoether acetate (PGMEA), 1-methoxy-2-propanol, propyleneglycol dimethyl ether, dipropyleneglycol butyl ether, dipropyleneglycol butyl ether acetate, tetrapropyleneglycol butyl ether, tripropylene glycol butyl ether, hexanol, heptanol, and combinations thereof. Depending on the application process, the solvent is present in the dopant in the range of from 0 weight percent (wt %) to about 70 wt. %. It will be appreciated that, during the processing, the order of addition of the components is immaterial. In accordance with yet another exemplary embodiment of the present invention, if the dopant is present in excess solvent, the mixture is concentrated by at least partial evaporation of the solvent or solvent mixture. In this regard, the concentration and viscosity of the resulting dopant can be controlled and increased. The solvent(s) may be evaporated using any suitable method such as, for example, permitting evaporation at or below room temperature, or heating the dopant mixture to temperatures at or above the boiling points of the solvent(s).

A functional additive also is added to the polyol-substituted silicon and the borate (step 20), in one embodiment. For example, a viscosity modifier that minimizes or prevents spreading of the dopant during, for example, screen printing, may be added. Examples of such viscosity-modifiers include glycerol, polyethylene glycol, polypropylene glycol, ethylene glycol/propylene glycol copolymer, organo-modified siloxanes, ethylene glycol/siloxane copolymers, polyelectrolyte, and the like, and combinations thereof. Examples of other suitable additives that may be added to the dopant include dispersants, surfactants, polymerization inhibitors, wetting agents, antifoaming agents, detergents and other surface-tension modifiers, flame retardants, pigments, plasticizers, thickeners, rheoloy modifiers, and mixtures thereof. It will be appreciated that a functional additive may serve one or more functions.

In another embodiment, the borate ester/the boron-comprising dopant has a concentration of transition metal cations of less than 100 parts per billion (ppb). Transition metal cations (e.g., Fe, Cr, Ni, and Cu) negatively affect "minority carrier lifetime," which is an important parameter for solar cells in photovoltaic applications. Transition metal cations affect carrier lifetime by providing recombination sites where electrons or holes can recombine rather than flowing to collectors of solar cells and contributing to the electricity generated by the cell. Longer carrier lifetime means a more efficient solar cell. Such low metal cation concentrations are possible by using purified borates and polyol-substituted silicon monomers to manufacture the borate esters/boron-comprising dopants. In a preferred embodiment, the borate ester/the boron-comprising dopant has a concentration of metal cations of less than 50 parts per billion (ppb).

The following are examples of borate esters/boron-comprising dopants fabricated as described above. The examples are provided for illustration purposes only and are not meant to limit the various embodiments of the present invention in any way.

EXAMPLE 1

A 1:1 Si:B molar ratio borate ester/boron-comprising dopant was prepared by combining 67.6 grams of tributyl borate with 80.0 grams of tetrakis(2-hydroxyethoxy)silane and 30.01 grams of 1-hexanol. The mixture was heated to 58° C., the pressure was reduced to 4-5 Torr, and the mixture was stirred until the resulting butanol was evaporated.

EXAMPLE 2

A 1.5:1 Si:B molar ratio borate ester/boron-comprising dopant was prepared by combining 45.7 grams of tributyl borate with 80.00 grams of tetrakis(2-hydroxyethoxy)silane and 20.01 grams of 1-hexanol. The mixture was heated to 58° C., the pressure was reduced to 4-5 Torr, and the mixture was stirred until the resulting butanol was evaporated. The viscosity was measured at 59.7 centipoise (cP).

EXAMPLE 3

A 2.5:1 Si:B molar ratio borate ester/boron-comprising dopant was prepared by combining 27.05 grams of tributyl borate with 80.00 grams of tetrakis(2-hydroxyethoxy)silane and 12.01 grams of 1-hexanol. The mixture was heated to 58° C., the pressure was reduced to 4-5 Torr, and the mixture was stirred until the resulting butanol was evaporated.

EXAMPLE 4

A 3:1 Si:B molar ratio borate ester/boron-comprising dopant was prepared by combining 22.53 grams of tributyl borate with 80.00 grams of tetrakis(2-hydroxyethoxy)silane and 10.0 grams of 1-hexanol. The mixture was heated to 58° C., the pressure was reduced to 4-5 Torr, and the mixture was stirred until the resulting butanol was evaporated. The viscosity was measured at 12.7 cP.

When the bottles were arranged in series and tilted simultaneously, the flow rates formed a clear sequence from slowest to highest in relation to the Si:B molar ratio:

TABLE 1

| Si:B | Wt. % B | Viscosity, Highest to lowest, Observed | Viscosity, Measured, cP × 1000 |
|---|---|---|---|
| 1:1 | 11.39 | 1 | — |
| 1.5:1 | 8.65 | 2 | 59.7 |
| 2.5:1 | 5.84 | 3 | — |
| 3:1 | 5.03 | 4 | 12.7 |

In another set of examples, boron esters/boron-comprising dopants with varying ratios of silicon to boron were formed and the sheet resistances of resulting doped silicon substrates were measured:

EXAMPLE 5

A 1.99:1 molar ratio borate ester/boron-comprising dopant was prepared by combining 14.08 grams of butyl borate with 40.00 grams of tetrakis(2-hydroxypropoxy)silane and 5.0 grams of 1-hexanol. The mixture was heated to 58° C., the pressure was reduced to 4-5 Torr, and the mixture was stirred until the resulting butanol was evaporated.

EXAMPLE 6

A 3.02:1 molar ratio borate ester/boron-comprising dopant was prepared by combining 9.28 grams of butyl borate with 40.00 grams of tetrakis(2-hydroxypropoxy)silane and 3.29 grams of 1-hexanol. The mixture was heated to 58° C., the pressure was reduced to 4-5 Torr, and the mixture was stirred until the resulting butanol was evaporated.

EXAMPLE 7

A 5.4:1 molar ratio borate ester/boron-comprising dopant was prepared by combining 5.18 grams of butyl borate with 40.00 grams of tetrakis(2-hydroxypropoxy)silane and 1.84 grams of 1-hexanol. The mixture was heated to 58° C., the pressure was reduced to 4-5 Torr, and the mixture was stirred until the resulting butanol was evaporated.

The products of all three borate ester/boron-comprising dopants were transparent viscous pastes. The pastes were screen-printed onto p-type silicon wafers, baked at 120° C. for two minutes, and then baked at 200° C. for two minutes. The wafers were heated in a furnace at 925° C. for sixty minutes to diffuse the boron and subjected to oxidation at 850° C. to remove the boron-rich layer (BRL). Subsequently, the remaining glass film was deglazed with dilute hydrofluoric acid. The sheet resistances of the doped wafers were then measured. The results are set forth in Table 2.

TABLE 2

| Wafer No. | Example No. | Si:B Ratio | Rs | Rs STD |
|---|---|---|---|---|
| 1 | 1 | 1.99:1 | 53.8 | 3.8 |
| 2 | 1 | 1.99:1 | 51.9 | 3.5 |
| 3 | 2 | 3.02:1 | 65.1 | 2.7 |
| 4 | 2 | 3.02:1 | 66.1 | 2.4 |
| 5 | 3 | 5.4:1 | 70.3 | 2.1 |
| 6 | 3 | 5.4:1 | 70.1 | 2.2 |

EXAMPLE 8

253.51 grams of butyl borate was combined with 449.97 grams of tetrakis(hydroxyethoxy)silane and 112.49 grams of 1-hexanol. The mixture was placed under vacuum at 3-5 torr and heated to 58° C. until the butanol was removed. 565.96 grams recovered. The levels of transition metals were determined by inductively-coupled mass spectrometry (ICP-MS):

TABLE 3

| Metal | Symbol | Concentration (ppb) |
|---|---|---|
| Chromium | Cr | 1.3 |
| Copper | Cu | 1.7 |
| Iron | Fe | 13 |
| Magnesium | Mg | 26 |
| Manganese | Mn | 0.43 |
| Nickel | Ni | 2.7 |

The borate ester/boron-comprising dopant was then used to coat 195 wafers by screen printing over a period of 5 hours. During printing the borate ester/boron-comprising dopant remained a transparent viscous liquid with no gellation or plugging of the screen.

Accordingly, methods of fabricating borate esters, boron-comprising dopants and methods of fabricating boron-comprising dopants have been provided. The borate esters and boron-comprising dopants are fabricated by the transesterification of borate using polyol-substituted silicon monomers, thus forming a boron and silicon network. Because the ester and dopant are formed using silicon monomers as opposed to polymers or oligomers used in conventional dopants, the synthesis of the ester and dopant is simple and the viscosity of the ester and dopant can be controlled and varied. By manipulating the mole ratio of silicon to boron, the viscosity and polarity can be controlled so that the dopant is suitable for a particular method of doping application. The ratio of boron to silicon also can be held constant and the viscosity and polarity varied by changing the amount of the second alcohol, and selecting polol-substituted silicates with different viscosities and polarity, and by optionally adding a solvent. The boron also is in a form with minimal outgassing from the dopant to the atmosphere and provides for maximum doping efficiency. The boron and silicon are dispersed uniformly throughout the ester network without pockets of high boron concentration or high silicon concentration. In addition, the molecular weight is stable at room temperature and, thus, the dopant can be used, transported, and stored at room temperature. Further, compared to sol-gel processing, the methods contemplated herein are simple and less costly.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A borate ester polymer comprising boron and silicon wherein the boron is linked to the silicon by alkyl groups that are bonded via ester bonds with both the boron and the silicon.

2. The borate ester polymer of claim 1, wherein the alkyl groups are derived from polyols selected from the group consisting pentaerythritol, pentane diol, glycerol, ethylene glycol, butane diol, and combinations thereof.

3. The borate ester polymer of claim 1, wherein the silicon and the boron are present at a mole ratio of from about 0.75:1 Si:B to about 6:1 Si:B.

4. The borate ester polymer of claim 3, wherein the silicon and the boron are present at the mole ratio of from about 1.5:1 Si:B to about 3:1 Si:B.

5. The borate ester polymer of claim 1, wherein the borate ester has the structure:

$$[(R^3)B]_y[(R^1)_n Si(R^2)_{(4-n)}]_x,$$

where $R^1$ is any diol or polyol or combination thereof, $R^2$ is any alkyl, aromatic, alkoxy, or phenoxy group, $R^3$ is tripropylene glycol butyl ether, heptanol, hexanol, propylene glycol methyl ether (PGME), dipropylene glycol methyl ether, di-propylene glycol propyl ether, di-propylene glycol butyl ether, butanol, pentanol, octanol, or decanol, n is 1, 2, 3, or 4, and x/y is equal to a value between 0.75 to 6.

6. A boron-comprising dopant comprising a boron and silicon network wherein the boron and the silicon are connected via Si—O-alkyl group-O—B linkages.

7. The boron-comprising dopant of claim 6, wherein the alkyl groups of the Si—O-alkyl group-O—B linkages are derived from polyols selected from the group consisting of pentaerythritol, pentane diol, glycerol, ethylene glycol, butane diol, and combinations thereof.

8. The boron-comprising dopant of claim 6, wherein the silicon and the boron are present at a mole ratio of from about 0.75:1 Si:B to about 6:1 Si:B.

9. The boron-comprising dopant of claim 8, wherein the silicon and the boron are present at the mole ratio of from about 1.5:1 Si:B to about 3:1 Si:B.

10. The boron-comprising dopant of claim 6, wherein the boron and silicon network has the structure:

$$[(R^3)B]_y[(R^1)_n Si(R^2)_{(4-n)}]_x,$$

where $R^1$ is any diol or polyol or combination thereof, $R^2$ is any alkyl, aromatic, alkoxy, or phenoxy group, $R^3$ is tripropylene glycol butyl ether, heptanol, hexanol, propylene glycol methyl ether (PGME), dipropylene glycol methyl ether, di-propylene glycol propyl ether, di-propylene glycol butyl ether, butanol, pentanol, octanol, or decanol, n is 1, 2, 3, or 4, and x/y is equal to a value between 0.75 to 6.

11. The boron-comprising dopant of claim 6, further comprising a solvent.

12. The boron-comprising dopant of claim 11, wherein the solvent is one selected from the group consisting of propylene glycol methyl ether (PGME), propylene glycol monoether acetate (PGMEA), 1-methoxy-2-propanol, propyleneglycol dimethyl ether, dipropyleneglycol butyl ether, dipropyleneglycol butyl ether acetate, tetrapropyleneglycol butyl ether, tripropylene glycol butyl ether, hexanol, heptanol, and combinations thereof.

13. The boron-comprising dopant of claim 6, wherein the boron-comprising dopant comprises less than 100 ppb of transition metal cations.

* * * * *